United States Patent [19]

Winter et al.

[11] 4,092,416
[45] May 30, 1978

[54] BENZOPYRONE DERIVATIVES EXHIBITING ANTI-ALLERGIC ACTIVITY

[75] Inventors: Werner Winter, Heppenheim; Max Thiel, Mannheim, both of Germany; Kurt Stach, deceased, late of Mannheim-Waldhof, Germany; Androniki Roesch, Mannheim; by Werner Plattner, administrator, Linz Austria; Wolfgang Schaumann, Heidelberg, both of Germany

[73] Assignee: Boehringer Mannheim GmbH, Mannheim, Germany

[21] Appl. No.: 746,551

[22] Filed: Dec. 1, 1976

[30] Foreign Application Priority Data

Dec. 9, 1975 Germany .................... 2555290

[51] Int. Cl.$^2$ ............... A61K 31/495; C07D 295/10
[52] U.S. Cl. ..................... 424/250; 260/592; 544/376; 544/399; 544/394; 544/374
[58] Field of Search ............... 260/268 BC; 424/250

[56] References Cited

U.S. PATENT DOCUMENTS 3,410,851  11/1968  Stauffer .................... 260/268 BC
4,001,280  1/1977   Umio et al. ................. 260/268BC Primary Examiner—Paul M. Coughlan, Jr.
Attorney, Agent, or Firm—Burgess, Dinklage & Sprung

[57] ABSTRACT

Benzopyrones of the formula

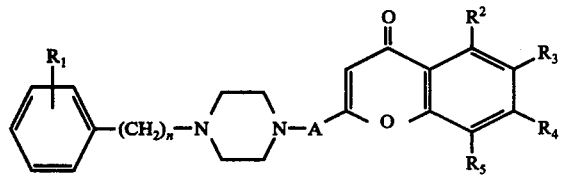

wherein
R$_1$ is a hydrogen or halogen atom or a hydroxyl, lower alkyl, alkoxy, alkylthio or trifluoromethyl radical,
R$_2$, R$_3$, R$_4$ and R$_5$ each independently is hydrogen, a halogen atom, a hydroxyl radical, a lower alkyl or lower alkoxy radical, or a lower alkyl or lower alkoxy radical substituted by at least one of hydroxyl, halogen, mesyloxy or tosyloxy or by an oxirane, dioxane or dioxolane ring,
A is a lower alkylene radical, and
$n$ is 0, 1 or 2,
and salts thereof exhibit anti-allergic activity.

10 Claims, No Drawings

BENZOPYRONE DERIVATIVES EXHIBITING ANTI-ALLERGIC ACTIVITY

The present invention is concerned with new benzopyrone derivatives and with the preparation thereof.

The benzopyrone derivatives according to the present invention are compounds of the general formula:

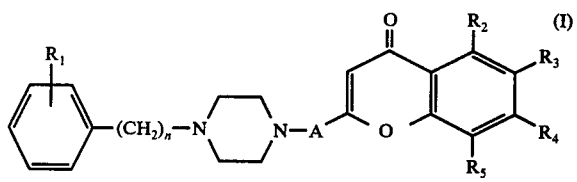

wherein $R_1$ is a hydrogen or halogen atom or a hydroxyl, lower alkyl, alkoxy, alkylthio or trifluoromethyl radical, $R_2$, $R_3$, $R_4$ and $R_5$, which may be the same or different, are hydrogen or halogen atoms or hydroxyl or lower alkyl radicals or lower alkoxy radicals optionally substituted one or more times by hydroxyl or halogen or by a mesyloxy or tosyloxy radical or by an oxirane, dioxane or dioxolane ring, A is a lower straight-chain or branched alkylene radical and $n$ is 0, 1 or 2; and the salts thereof with pharmacologically compatible acids.

By lower alkyl, lower alkoxy and lower alkylthio radicals as substituents $R_1$, $R_2$, $R_3$, $R_4$ and $R_5$, there are to be understood radicals containing up to 6 and preferably up to 3 carbon atoms. The lower alkyl radical is preferably a methyl radical.

Halogen is a fluorine, chlorine or bromine atom and preferably a chlorine atom.

The dioxane ring is preferably a 1,3-dioxane ring.

The lower, straight-chain or branched alkylene radical A can contain up to 4 carbon atoms and is preferably a methylene, ethylene, n-propylene, n-butylene, methylmethylene, methylethylene, methylpropylene, dimethylmethylene or dimethylethylene radical.

The benzopyrones of general formula (I) have an anti-allergic activity which has been demonstrated by passive cutaneous anaphylaxis in rats. They also possess an inhibiting influence on intradermally injected histamine. Furthermore, we have found that compounds of general formula (I) are valuable intermediates for the synthesis of pharmaceutically-useful compounds.

The compounds according to the present invention can be prepared, for example, by one of the following methods:

(a) reaction of a 2-hydroxy-acetophenone of the general formula:

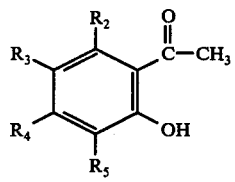

wherein $R_2$, $R_3$, $R_4$ and $R_5$ have the same meanings as above, with a piperazinyl-fatty acid ester of the general formula:

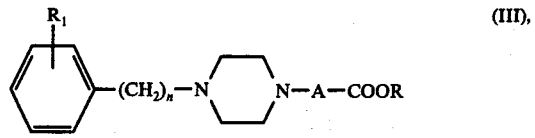

wherein $R_1$, A and $n$ have the same meanings as above and R is a lower alkyl radical; or (b) reaction of a compound of the general formula:

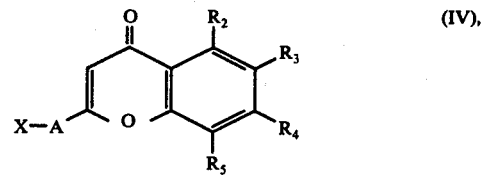

wherein A, $R_2$, $R_3$, $R_4$ and $R_5$ have the same meanings as above and X is a reactive group, with a piperazine derivative of the general formula:

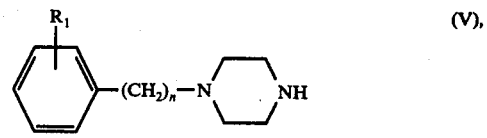

wherein $R_1$ and $n$ have the same meanings as above, optionally with the intermediate protection of the hydroxyl groups, and, when $R_1$, $R_2$, $R_3$, $R_4$ and/or $R_5$ are hydroxyl or alkoxy radicals, these radicals can be subsequently converted into one another and subsequently, if desired, either the salt obtained under the reaction conditions is converted into the free base of general formula (I) or the free base is converted into a pharmacologically compatible acid-addition salt.

The lower alkyl radical substituent R in compounds of general formula (III) can contain up to 6 and preferably up to 4 carbon atoms, the methyl and ethyl radicals being preferred.

Reactive derivatives of general formula (IV) include the halides and the mesyloxy and tosyloxy compounds.

The process (a) according to the present invention for the preparation of compounds of general formula (I) is carried out by the known Claisen condensation in which a 2-hydroxy-acetophenone of general formula (II) is first reacted with a piperazinyl-fatty acid ester of general formula (III) in the presence of an alkaline condensation agent to give a 1,3-diketone of general formula (VI) or the tautomer thereof of general formula (VII):

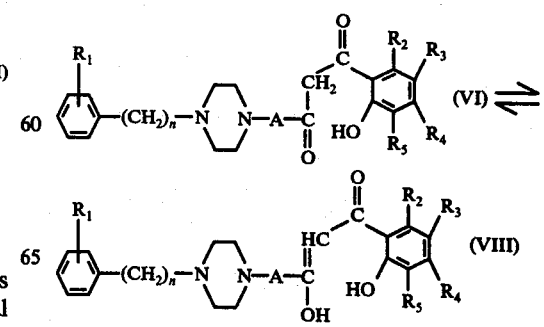

wherein $n$, $R_1$, $R_2$, $R_3$, $R_4$ and $R_5$ have the same meanings as above.

These 1,3-diketones are subsequently cyclized under acidic reaction conditions, by splitting off water, to give the desired benzopyrone derivatives.

The 1,3-diketones of general formula (VI) and their tautomers of general formula (VII) are new and can be isolated as their sodium salts.

The alkaline condensation agents used can be the metals, metal hydroxides, metal hydrides, alcoholates and the like known from the literature for the Claisen condensation, using appropriate solvents, such as alcohols, non-reactive aromatics, dioxane, strongly polar aprotic solvents, such as hexametapol and the like; depending upon the solubility of the reaction components, non-polar solvents, such as ligroin and other petroleum fractions, can also be used.

The ring closure reaction takes place in an acidic medium, preferably with aqueous hydrochloric acid, alcoholic hydrochloric acid, dioxane, polyphosphoric acid, glacial acetic acid or concentrated sulfuric acid, or under mild conditions with, for example, polyphosphoric acid esters.

Various variants of the Claisen condensation can also be used. Thus, for example, the phenolic hydroxyl group of the 2-hydroxyacetophenones of general formula (II) can be temporarily blocked by a protective group which is easily split off, as can the substituents of $R_2$, $R_3$, $R_4$ or $R_5$ when these represent hydroxyl groups. Preferred protective groups include the formyl and tetrahydropyranyl radicals.

When, in these compounds, $R_2$, $R_3$, $R_4$ or $R_5$ signify alkoxy radicals substituted by hydroxyl, the alcoholic hydroxyl group can also be protected by the abovementioned manner.

Furthermore, when $R_2$, $R_3$, $R_4$ or $R_5$ in compounds of general formula (II) signifies a poly-hydroxylated alkoxy radical, this radical, in addition to the already protected phenolic hydroxyl group, can be protected with aldehydes or ketones by the formation of a dioxane or dioxolane ring.

The above-mentioned protective groups are usually split off by the acidic medium used for the ring closure reaction. However, the splitting off can also be carried out by aqueous acidic hydrolysis, with, for example, hydrochloric acid or sulfuric acid.

Further special process variants for preparing compounds of general formula (I), wherein $R_2 - R_5$ signify alkoxy radicals optionally substituted by hydroxyl or halogen or by an oxirane ring, include subsequently alkylating compounds of general formula (I), in which $R_2 - R_5$ signify hydroxyl groups, with an appropriately substituted haloalkyl compound or with, for example, a corresponding mesyloxy or tosyloxy compound.

A further process variant for the preparation of compounds of general formula (I), wherein $R_2 - R_5$ can be hydroxyl groups, comprises synthesizing compounds of general formula (I), wherein $R_2 - R_5$ are lower alkoxy radicals, and subsequently dealkylating in known manner, for example under mild conditions with boron tribromide.

Some of the piperazinyl-fatty acid esters used, as well as some of the 2-hydroxy-acetophenones optionally provided with protective groups, are new compounds. Their preparation is described in the following Examples.

The process (b) is carried out in such a manner that, first, according to process (a), a 2-hydroxyacetophenone of general formula (II) is subjected to a Claisen condensation with an appropriate hydroxy-fatty acid ester, the hydroxyl group of which is protected, the reaction product is cyclized in an acidic medium, with the splitting off of water, the 2-hydroxyalkylbenzpyrone compound obtained is converted into a reactive compound of general formula (IV) and this product is reacted with a piperazine derivative of general formula (V).

The pharmacologically compatible salts are obtained in the usual way, for example by neutralization of compounds of general formula (I) with a non-toxic inorganic or organic acid, for example, hydrochloric acid, sulfuric acid, phosphoric acid, hydrobromic acid, acetic acid, lactic acid, citric acid, malic acid, salicylic acid, malonic acid, maleic acid or succinic acid.

The new compounds of general formula (I) according to the present invention and the salts thereof can be administered enterally and parenterally in liquid or solid form, employing the usual forms of administration, for example, tablets, capsules, dragees, syrups, solutions or suspensions. As injection medium, water is preferably employed which contains the additives usual in the case of injection solutions, such as stabilizing agents, solubilizing agents and buffers. Additives of this type include, for example, tartrate and citrate buffers, ethanol, complex formers (such as ethylenediaminetetraacetic acid and its non-toxic salts) and high molecular weight polymers (such as liquid polyethylene oxide) for viscosity regulation. Liquid carrier materials for injection solutions must be sterile and are preferably filled into ampules. Solid carrier materials include, for example, starch, lactose, mannitol, methyl cellulose, talc, highly dispersed silicic acid, high molecular weight fatty acids (such as stearic acid), gelatin, agar-agar, calcium phosphate, magnesium stearate, animal and vegetable fats and solid high molecular weight polymers (such as polyethylene glycols); compositions suitable for oral administration can, if desired, contain flavoring and sweetening materials.

The following Examples are given for the purpose of illustrating the present invention:

EXAMPLE 1

2-{2-[4-(2-Methoxyphenyl)-piperazinyl-1-]-ethyl}-5-methoxy-4-oxo-4H-1-benzopyran (a) 2-Hydroxy-6-methoxy-acetophenone 126.3 g. (0.83 mol) 2,6-dihydroxyacetophenone are dissolved in 900 ml acetone, mixed with 229.4 g (1.66 mol) potassium carbonate and, after the addition of 141.9 g (1 mol) methyl iodide heated to the boil for 3 hours. Subsequently, the reaction mixture is heated with suction, the mother liquor is evaporated in a vacuum, the residue is taken up in diethyl ether and phenolic components are removed by shaking out with 2N aqueous sodium hydroxide solution. The aqueous alkaline layer is then acidified with 2N hydrochloric acid and extracted with diethyl ether. The ethereal solution is evaporated to give 131 g (95% of theory) of practically pure 2-hydroxy-6-methoxy-acetophenone; m.p. 53° – 54° C.

(b) Ethyl 3-[4-(2-methoxyphenyl)-piperazinyl-1]-propionate

To a solution of 30.0 g. (0.3 mol) ethyl acrylate in 100 ml ethanol are added dropwise a solution of 57.7 g (0.3 mol) 1-(2-methoxyphenyl)-piperazine in 100 ml ethanol.

The reaction mixture is stirred for 3 hours at ambient temperature and subsequently evaporated, whereafter the residue is distilled in a high vacuum. There are obtained 75.9 g (86.5% of theory) ethyl 3-[4-(2-methoxyphenyl)-piperazinyl-1]-propionate; b.p. 163° C/0.01 mm Hg.

(c)
1-{2-[4-(2-Methoxyphenyl)-piperazinyl-1]-ethyl}-3-(2-hydroxy-6-methoxyphenyl)-propane-1,3-dione 7.2 g sodium hydride (0.3 mol) in the form of a 50% commercially available dispersion are suspended in 100 ml dry dioxane and heated to 80° C, while stirring. Subsequently, a solution of 16.6 g (0.1 mol) 2-hydroxy-6-methoxy-acetophenone, prepared according to Example 1a, and 34.2 g (0.11 mol) ethyl 3-[4-(2-methoxyphenyl)-piperazinyl-1]-propionate, prepared according to Example 1b, in 75 ml dioxane is added dropwise at 80° – 90° C to the sodium hydride suspension, followed by heating under reflux for 1 hour, whereafter the reaction mixture is allowed to cool. The reaction mixture is thereafter stirred into 1 liter ligroin. As intermediate product of general formula (IV), there precipitates out the yellowish colored, amorphous sodium salt of 1-{2-[4-(2-methoxyphenyl)-piperazinyl-1]-ethyl}-3-(2-hydroxy-6-methoxyphenyl)-propane-1,3-dione, which is washed with ligroin and diethyl ether. The yield is 36.9 g. (85% of theory).

(d)
2-{2-[4-(2-Methoxyphenyl)-piperazinyl-1]-ethyl}-5-methoxy-4-oxo-4H-1-benzopyran 36.5 g of the propane-1,3-dione prepared according to Example 1c are dissolved in 250 ml ethanol, then cooled to 0° C and saturated with gaseous hydrogen chloride, followed by stirring for 0.5 hours. The slurry-like mass obtained is poured on to ice and neutral contaminants are removed by shaking out with methylene chloride. The aqueous phase is neutralized by the addition of solid sodium bicarbonate, followed by again extracting with methylene chloride. The organic phase is thereafter dried and evaporated and the residue is taken up in dry tetrahydrofuran and mixed with ethereal hydrochloric acid. The hydrochloride of 2-{2-[4-(2-methoxyphenyl)-piperazinyl-1]-ethyl}-5-methoxy-4-oxo-4H-1-benzopyran precipitates out and is filtered off with suction and dried in a desiccator. The product, which is chromatographically pure, is in the form of a mixture of the mono- and dihydrochlorides; m.p. 129° – 134° C (decomposition). The yield is 36.6 g (about 75% of theory).

The structure is clearly demonstrated spectroanalytically by IR, UV, NMR and mass spectra. UV: 316 mµ (MeOH), 321 mµ (pH 1), 320 mµ (pH 13) NMR (DDMSO): 3-H; 6.16 ppm; singulet.

A part of the product is triturated with a little methanol. After initial dissolving, the pure dihydrochloride crystallizes out; m.p. 192° C (1% by weight water content).

From a sample of the hydrochloride mixture, the base is liberated with sodium bicarbonate and, after the addition of diethyl ether or ligroin, is obtained in crystalline form; m.p. 120° – 121° C.

In the case of different batches, hydrochlorides of greatly differing water content are obtained, which extended up to 12% by weight.

The dihydrochloride of the product obtained according to Example 1d loses one mol hydrochloric acid relatively easily, depending upon the temperature in the drying process.

EXAMPLE 2

2-[2-(4-Phenylpiperazinyl-1)-ethyl]-5-methoxy-4-oxo-4H-1-benzopyran (a) 63 g (0.39 mol) phenylpiperazine and 41.8 g (0.39 mol) ethyl acrylate are reacted in 270 ml ethanol according to Example 1b to give 87.5 g (85.9% of theory) ethyl 3-(4-phenyl-piperazinyl-1)-propionate; b.p. 140° – 145° C/0.01 mm Hg.

(b) Analogously to Example 1c, 3.6 g (0.15 mol) sodium hydride, 8.3 g (0.05 mol) 2-hydroxy-6-methoxyacetophenone (see Example 1a) and 14.4 g (0.055 mol) ethyl 3-(4-phenylpiperazinyl-1)-propionate (see Example 2a) are reacted in 100 ml dioxan. The sodium salt of 1-[2-(4-phenylpiperazinyl-1)-ethyl]-3-(2-hydroxy-6-methoxyphenyl)-propane-1,3-dione is isolated by dilution with ligroin.

(c) The still ligroin-moist sodium salt obtained in Example 2b is, analogously to Example 1d, dissolved in 70 ml ethanol and acidified with 40 ml ethanolic hydrochloric acid. The reaction mixture is stirred for 1 hour at ambient temperature, saturated with gaseous hydrogen chloride at 0° C and thereafter stirred at 50° C. The reaction mixture is poured on to ice and extracted with methylene chloride. The desired product is isolated from the organic phase in the form of the mono-hydrochloride, a further amount being obtained by neutralization of the aqueous phase. The products are combined and converted, via an acid/weakly alkaline working up, into the dihydrochloride. There are obtained 2-[2-(4-phenylpiperazinyl-1)-ethyl]-5-methoxy-4-oxo-4H-1-benzopyran dihydrochloride in a yield of 14.6 g (61% of theory) (10% by weight water content); m.p. 135° – 137° C.

A sample of this product is converted into the free base with aqueous sodium bicarbonate solution; m.p. 122.5° – 123° C (recrystallized from ethyl acetate/ligroin).

As in Example 1, the structural proof was obtained by spectral analysis:

UV: 316 mµ (MeOH), 321 mµ (PH 7), 322 mµ (pH 1), 321 mµ (pH 13).

EXAMPLE 3

2-{2-[4-(2-Chlorophenyl)-piperazinyl-1]-ethyl}-5-methoxy-4-oxo-4H-1-benzopyran Analogously to Example 1a – d, the chlorophenylpiperazine derivative and the corresponding intermediate compounds are prepared: ethyl 3-[4-(2-chlorophenyl)-piperazinyl-1]-propionate from ethyl 2-chlorophenyl-piperazine and ethyl acrylate; b.p. 152° – 154° C/0.01 mm Hg. Yield: 92.4% of theory.

After the ring closure reaction with ethanolic hydrochloric acid, the reaction mixture is extracted with chloroform. The desired compound is isolated in the form of the monohydrochloride from the organic phase as the main product. The aqueous phase is subsequently mixed with solid sodium bicarbonate and the precipitated crude base is combined with the monohydrochloride and together converted into the dihydrochloride via an acidic/weakly basic working up. There is obtained 2-{2-[4-(2-chlorophenyl)-piperazinyl-1]-ethyl}-5-methoxy-4-oxo-4H-1-benzopyran dihydrochloride; m.p. 182° C. (8% by weight water content). Yield: 13.6 g (about 55% of theory).

EXAMPLE 4

2-{2-[4-(2-Ethoxyphenyl)-piperazinyl-1]-ethyl}-5-methoxy-4-oxo-4H-1-benzopyran

Analogously to Example 1a – d, using ethyl 3-[4-(2-ethoxyphenyl)-piperazinyl-1]-propionate (prepared analogously to Example 1b; b.p. 162° – 164° C/0.01 mm Hg; yield: 94.4% of theory), there is obtained, as in Examples 1 – 3, by reaction with 2-hydroxy-6-methoxy-acetophenone, 2-{2-[4-(2-ethoxyphenyl)-piperazinyl-1]-ethyl}-5-methoxy-4-oxo-4H-1-benzopyran in the form of the monohydrochloride; m.p. 118° – 120° C (9.5% by weight water content). Yield: 53% of theory.

EXAMPLE 5

2-{2-[4-(4-Methoxyphenyl)-piperazinyl-1]-ethyl}-5-methoxy-4-oxo-4H-1-benzopyran

With the use of ethyl 3-[4-(4-methoxyphenyl)-piperazinyl-1]-propionate (prepared analogously to Example 1b; b.p. 170° – 175° C/0.01 mm Hg; m.p. 53° C; yield: 93% of theory), there is obtained, as in Examples 1 – 3, by reaction with 2-hydroxy-6-methoxy-acetophenone, 2-{2-[4-(4-methoxyphenyl)-piperazinyl-1]-ethyl}-5-methoxy-4-oxo-4H-1-benzopyran in the form of the dihydrochloride (13% by weight water content after freeze drying of the aqueous solution); m.p. 140° – 143° C. Yield: 50% of theory.

The water content corresponds to 4 mol water of crystallization. The base, precipitated out with aqueous bicarbonate solution, melts, in analytically pure form, at 123° – 124° C.

The dihydrochloride (m.p. 211° C) can be isolated from a mixture of tetrahydrofuran/diethyl ether.

The spectrol-analytical structural proof is carried out analogously to Example 1.

EXAMPLE 6

2-{2-[4-(3-Methoxyphenyl)-piperazinyl-1]-ethyl}-5-methoxy-4-oxo-4H-1-benzopyran (a) Analogously to Example 1b, by the reaction of 50 g 1-(3-methoxyphenyl)-piperazine with acrylic acid, there are obtained 57.5 g (75.64% of theory) ethyl 3-[4-(3-methoxyphenyl)-piperazinyl-1]-propionate; b.p. 211° – 212° C/0.1 – 0.2 mm Hg (slightly overheated).

(b) Chromone ring closure is carried out analogously to Example 1; 8.3 g (0.05 mol) 2-hydroxy-6-methoxyacetophenone are reacted with 16.08 g (0.055 mol) of the propionic acid ester prepared according to Example 6a in the presence of 3.6 g sodium hydride in dioxane. The reaction mixture is extracted with methylene chloride. In this way, there is obtained a hydrochloride melting at 126° C (17.9 g. crude yield; 76.7% of theory). Because of the high water content of the salt, it can be stirred up with about 75 ml isopropanol. The greater part of the substance thereby goes into solution and crystallizes out again after a short time. There are obtained 13.8 g 2-{2-[4-(3-methoxyphenyl)-piperazinyl-1]-ethyl}-5-methoxy-4-oxo-4H-1-benzopyran dihydrochloride (59% of theory); m.p. 146° – 148° C.

EXAMPLE 7

2-{2-[4-(2-Methylphenyl)-piperazinyl-1]-ethyl}-5-methoxy-4-oxo-4H-1-benzopyran

With the use of ethyl 3-[4-(2-methylphenyl)-piperazinyl-1]-propionate (prepared analogously to Example 1b; b.p. 147° C/0.01 mm Hg; yield: 69% of theory), there is obtained, according to the method described in Examples 1 – 3, by reaction with 2-hydroxy-6-methoxy-acetophenone, 2-{2-[4-(2-methylphenyl)-piperazinyl-1]-ethyl}-5-methoxy-4-oxo-4H-1-benzopyran in the form of the analytically pure dihydrochloride; m.p. 161° – 162° C (recrystallized from isopropanol) in 56% yield.

The structure is ascertained spectro-analytically as in Example 1 (e.g. mass spectrum).

EXAMPLE 8

2-{2-[4-(2-Methoxyphenyl)-piperazinyl-1]-ethyl}-4-oxo-4H-1-benzopyran

According to the method described in Examples 1 – 3, 13.5 g (0.1 mol) commercially-available 2-hydroxyacetophenone and 34.2 g (0.11 mol) ethyl 3-[4-(2-methoxyphenyl)-piperazinyl-1]-propionate (see Example 1b) are reacted in the presence of 4.8 g (0.2 mol) sodium hydride in 100 ml dioxane. There is obtained 2-{2-[4-(2-methoxyphenyl)-piperazinyl-1]-ethyl}-4-oxo-4H-1-benzopyran in the form of the analytically pure dihydrochloride; m.p. 197° C. The yield is 26.63 g (60.9% of theory).

The structure is ascertained spectro-analytically as in Example 1; UV (MeOH): 291 mμ; 301 mμ (pH 1); 299 mμ (pH 13).

EXAMPLE 9

2-{2-[4-(2-Methoxyphenyl)-piperazinyl-1]-ethyl}-7-methoxy-4-oxo-4H-1-benzopyran (a) Analogously to Example 1a, 152.15 g (1 mol) 2,4-dihydroxyacetophenone, 246 g (2 mol) potassium bicarbonate and 170 g (1.2 mol) methyl iodide are heated to the boil in 900 ml acetone for 3 hours. After the same working up, there are obtained 141.3 g (85% of theory) 2-hydroxy-4-methoxy-acetophenone; m.p. 52° C.

(b) According to the method described in Example 1, by the reaction of 2-hydroxy-4-methoxy-acetophenone (see Example 9a) with ethyl 3-[4-(2-methoxyphenyl)-piperazinyl-1]-propionate (see Example 1b), there is obtained 2-{2-[4-(2-methoxyphenyl)-piperazinyl-1]-ethyl}-7-methoxy-4-oxo-4H-1-benzopyran in the form of its dihydrochloride; m.p. 205° C. The yield is 58% of theory. The free base melts at 154° C.

EXAMPLE 10

2-{2-[4-(2-Methoxyphenyl)-piperazinyl-1]-ethyl}-6-chloro-4-oxo-4H-1-benzopyran

According to the method described in Example 1, from 17 g (0.1 mol) 2-hydroxy-5-chloroacetophenone (see K. V. Auwers, C. Wittig, Berichte, 57, 1274/1924) and 34.2 g (0.11 mol) ethyl 3-[4-(2-methoxyphenyl)-piperazinyl-1]-propionate, there are obtained 26.9 g (62% of theory) 2-{2-[4-(2-methoxyphenyl)-piperazinyl-1]-ethyl}-6-chloro-4-oxo-4H-1-benzopyran in the form of the monohydrochloride; m.p. 205° – 207° C.

The structure is ascertained spectro-analytically as in Example 1; UV: 311 mμ (MeOH), 310 mμ (pH 1), 308 mμ (pH 13).

EXAMPLE 11

2-{2-[4-(2-Methoxyphenyl)-piperazinyl-1]-ethyl}-6-methyl-4-oxo-4H-1-benzopyran

According to the method described in Example 1 but with the use of a mixture of tetrahydrofuran/hexamethylphosphoric acid triamide (8:2), 15 g (0.1 mol) 2- hydroxy-5-methylacetophenone and 34.2 g (0.11 mol) ethyl 3-[4-(2-methoxyphenyl)-piperazinyl-1]-propionate are reacted at a temperature of 60° – 65° C. There is obtained, 61% yield, 2-{2-[4-(2-methoxyphenyl)-piperazinyl-1]-ethyl}-6-methyl-4-oxo-4H-1-benzopyran in the form of the monohydrochloride; m.p. 173° – 175° C. The corresponding dihydrochloride melts at 199° – 201° C.

The structure is ascertained, as usual, spectro-analytically and the purity is controlled by thin layer chromatography (solvent mixture isopropanol/butyl acetate/water/concentrated aqueous ammonia solution: 50/30/15/5).

EXAMPLE 12

2-[4-(2-Methoxyphenyl)-piperazinyl-1-methyl]-5-methoxy-4-oxo-4H-1-benzopyran (a) 38.4 g (0.2 mol) 2-methoxyphenylpiperazine are dissolved in 250 ml tetrahydrofuran and 60.7 g (0.6 mol) triethylamine. To this solution is added dropwise, at ambient temperature, 33.4 g (0.2 mol) ethyl bromoacetate. The reaction, which is strongly exothermic, is ended after 15 minutes. Thereafter, the reaction mixture is filtered off with suction, the filtrate is evaporated to remove the solvent and the residue is distilled in a high vacuum to give ethyl 4-(2-methoxyphenyl)-piperazinyl-1-acetate in 81% yield (45.3 g ); b.p. 149° – 158° C/0.1 mm Hg.

(b) The acetic acid derivative prepared according to Example 12a is reacted according to Example 1 – 3. From 12.46 g (0.075 mol) 2-hydroxy-6-methoxy-acetophenone and 22.26 g (0.08 mol) of the ester obtained in Example 12a, there are obtained 23.7 g (69.7% of theory) 2-[4-(2-methoxyphenyl)-piperazinyl-1-methyl]-5-methoxy-4-oxo-4H-1-benzopyran in the form of the dihydrochloride; m.p. 209° – 211° C.

EXAMPLE 13

2-{2-[4-(4-Chlorobenzyl)-piperazinyl-1]-ethyl}-5-methoxy-4-oxo-4H-1-benzopyran (a) Analogously to Example 1a, 30 g (0.3 mol) ethyl acrylate and 63.2 g 1-(4-chlorobenzyl)-piperazine are reacted in 200 ml ethanol to give 86.5 g (92.8% of theory) ethyl 3-[4-(4-chlorobenzyl)-piperazin-1-yl]-propionate; b.p. 150° – 160° C./0.1 mm Hg.

(b) From 24.9 g (0.15 mol) 2-hydroxy-6-methoxy-acetophenone and 51.3 g (0.16 mol) of the propionic acid derivative of Example 13a, there are obtained, by reaction with 10.8 g (0.45 mol) sodium hydride in 260 ml dioxan analogously to Example 1, 54 g (74.1% of theory) 2-{2-[4-(4-chlorobenzyl)-piperazinyl-1]-ethyl}-5-methoxy-4-oxo-4H-1-benzopyran in the form of the dihydrochloride; m.p. 247° C (decomposition).

The structure is ascertained by spectral analysis, including the mass spectrum (found 412).

EXAMPLE 14

2-{2-[4-(4-Chlorobenzyl)-piperazinyl-1]-ethyl}-5-hydroxy-4-oxo-4H-1-benzopyran 9.8 g (0.02 mol) of the 5-methoxy-benzopyran described in Example 13 are suspended in 200 ml chloroform and mixed at —20° C with a solution of 10 g (0.04 mol) boron tribromide in 100 ml chloroform. The reaction mixture is subsequently allowed to warm up to ambient temperature, again mixed with 5 g boron tribromide in 25 ml chloroform and thereafter stirred for 2 hours. Excess boron tribromide is thereafter decomposed by the addition of methanol. The solid product is isolated by suction filtration, mixed with aqueous bicarbonate solution and the benzopyran isolated by chloroform extraction. After the addition of etheral hydrochloric acid, there are obtained 6.2 g (65.8% of theory) 2-{2-[4-(4-chlorobenzyl)-piperazinyl-1]-ethyl}-5-hydroxy-4-oxo-4H-1-benzopyran; m.p. > 260° C (decomposition).

From the mother liquor of the solid product, there is obtained a further 0.8 g (8.5% of theory) of the desired product.

The structure is ascertained spectro-analytically, the mass of 398 is confirmed and the phenolic group is ascertained, inter alia, by the UV spectrum.

UV 330 m$\mu$ (MeOH), 368 m$\mu$ (pH 13).

EXAMPLE 15

2-{2-[4-(2-Methoxyphenyl)-piperazinyl-1]-ethyl}-5-hydroxy-4-oxo-4H-1-benzopyran (a) 90.6 g (0.6 mol) 2,6-dihydroxyacetophenone are suspended in 200 ml 2,3-dihydro-4H-pyran and mixed with a drop of polyphosphoric acid. After a few minutes, heating occurs, and the starting material dissolves. The reaction mixture is left to stand overnight, then mixed with diethyl ether and shaken out with 2N aqueous sodium hydroxide solution. The ethereal layer is dried and evaporated. There are obtained 72 g crude 2,6-bis-(tetrahydropyran-2-yloxy)-acetophenone in the form of a very viscous oil.

The aqueous alkaline layer is mixed with solid carbon dioxide and the yellowish precipitate obtained is extracted with diethyl ether. The ethereal extract is dried and evaporated. There are obtained 110 g 2-hydroxy-6-(tetrahydropyran-2-yloxy)-acetophenone.

The mono- as well as the di-(tetrahydropyran-2-yloxy derivative can be used in the present form for the further reaction.

(b) 23.6 g (about 0.1 mol) of the 2-hydroxy-6-(tetrahydropyran-2-yloxy)-acetophenone described in Example 15a are reacted with 34.16 g (0.11 mol) ethyl 3-[4-(2-methoxyphenyl)-piperazinyl-1]-propionate (see Example 1b) in the presence of 7.2 g (0.3 mol) sodium hydride in 170 ml dioxane as described in Example 2. After the usual working up, the combined chloroform extracts are treated with aqueous sodium bicarbonate solution. There is obtained, in over 90% yield, 2-{2-[4-(2-methoxyphenyl)-piperazinyl-1]-ethyl}-5-hydroxy-4-oxo-4H-1-benzopyran; m.p. 113° – 115° C. A sample is converted into the corresponding dihydrochloride; m.p. 188° – 190° C (decomposition) (3% by weight water content).

The structure is ascertained by spectral analysis; UV: 329 m$\mu$ (meOH), 329 m$\mu$ (pH 1), 368 m$\mu$ (pH 13). The mass is ascertained by the mass spectrum as being 380.

EXAMPLE 16

2-{2-[4-(2-Methoxyphenyl)-piperazinyl-1]-ethyl}-5-(2,3-dihydroxypropoxy)-4-oxo-4H-1-benzopyran (a)
2,2-Dimethyl-4-(2-acetyl-3-hydroxyphenoxymethyl)-dioxalane 1,3

11.3 g. (0.05 mol) of the 2-hydroxy-6-(2,3-dihydroxypropoxy)-acetophenone (m.p. 88° – 92° C) prepared, analogously to Example 1a, by the reaction of 2,6-dihydroxyacetophenone with 1-chloro- or 1-bromopropane-2,3-diol, are dissolved, together with 20.8 g (0.2 mol) acetone dimethyl acetal, in 150 ml tetrahydrofuran, with the addition of 20 ml dioxan containing hydrogen chloride. Thereafter, the reaction mixture is partly evaporated, the residue is stirred into aqueous ammonium carbonate solution, the precipitated oil is separated by decantation and the product is taken up in ethyl acetate and diethyl ether. By way of a 2N aqueous sodium hydroxide solution, by the addition of solid carbon dioxide, there are precipitated 10.9 g (82% of theory) chromatographically almost pure 2,2-dimethyl-4-[(2'-acetyl-3'-hydroxyphenoxy)-methyl]-dioxalane-1,3; m.p. 56° – 58° C.

(b) Chromone ring closure

As described in Examples 1 – 3, 10.9 g of the dioxalane-1,3 derivative described in Example 16a is subjected to chromone ring closure with ethyl 3-[4-(2-methoxyphenyl)-piperazinyl-1]-propionate, with the simultaneous splitting off of acetone. There is obtained the hydrochloride of 2-{2-[4-(2-methoxyphenyl)-piperazinyl-1]-ethyl}-5-(2,3-dihydroxypropoxy)-4-oxo-4H-1-benzopyran (14 g = 64.9% of theory).

Thermoanalysis shows a melting point of 137° C at a water content of 9.5% by weight.

The structure is ascertained, inter alia, by the mass spectrum which, after acetylation, shows the mole peak of the diacetyl derivative of 538 (M.W. + 84). UV: 315 mµ (MeOH); 319 mµ (pH 1); 319 mµ (pH 13).

EXAMPLE 17

2-{2-[4-(2-Methoxybenzyl)-piperazinyl-1]-ethyl}-5-methoxy-4-oxo-4H-1-benzopyran (a) Ethyl 1-(2-methoxybenzyl)-piperazinyl-4-carboxylate 94.8 g ethyl piperazine-N-carboxylate are catalytically hydrogenated with 243 g 2-methoxy-benzaldehyde in 300 ml ethanol in the presence of Raney nickel for 5 hours at 50° C and 50 atmospheres hydrogen pressure. After purification via the hydrochloride, there is obtained the desired product in the form of an oil which, as crude product (chromatographically almost pure) is further worked up. Yield: 110.2 g (66% of theory).

(b) 1-(2-Methoxybenzyl)-piperazine

The N-carboxylic acid ester obtained according to Example 17a is heated under reflux for 70 hours with 105 g potassium hydroxide in 1000 ml ethanol. The still warm reaction mixture is acidified with concentrated hydrochloric acid and thereafter stirred for 30 minutes. Subsequently, the bulk of the ethanol is evaporated off, the residue is mixed with 10N aqueous sodium hydroxide solution and the oil obtained is isolated and distilled in a vacuum. There are obtained 62.5 g (72.56% of theory) pure 1-(2-methoxybenzyl)-piperazine; b.p. 162° – 168° C/0.01 mm Hg.

(c) Ethyl 3-[4-(2-methoxybenzyl)-piperazin-1-yl]-propionate

Analogously to Example 1b, 58 g of the piperazine derivative prepared according to Example 17b are reacted with an equimolar amount of ethyl acrylate in 200 ml ethanol to give the desired basic propionic acid ester in 72.6% yield (62.5 g.); b.p. 162° – 168° C/0.01 mm Hg.

(d) Chromone ring closure 8.3 g (0.05 mol) 2-hydroxy-6-methoxy-acetophenone (prepared according to Example 1a) are reacted with 16.85 g (0.055 mol) ethyl 3-[4-(2-methoxybenzyl)-piperazin-1-yl]-propionate (prepared according to Example 17c) in 90 ml dioxane. After working up as in Examples 1 – 3 (in this case, with methylene chloride as extraction agent), there are obtained 21 g (80% of theory) 2-{2-[4-(2-methoxybenzyl)-piperazinyl-1]-ethyl}-5-methoxy-4-oxo-4H-1-benzopyran in the form of the dihydrochloride (water content 12.5% by weight); m.p. 134° C (decomposition; strong sintering above 120° C A sample of the substance is converted, from chloroform, via the base, into the dihydrochloride; m.p. 211° – 213° C (0.6% by weight water content).

Besides the elementary analysis, spectro-analytical data are utilized, as in Example 1, for proof of structure; UV: 314 mµ (MeOH), 320 mµ (pH 7), 321 mµ (pH 1), 319 mµ (pH 13).

EXAMPLE 18

2-{2-[4-(2-Methoxyphenyl)-piperazinyl-1]-ethyl}-5,7-dimethyl-4-oxo-4H-1-benzopyran From 8.21 g (0.05 mol) 4,6-dimethyl-2-hydroxy-acetophenone, there is obtained, according to Examples 1 – 3, by reaction with 16.08 g (0.055 mol) ethyl 3-[4-(2-methoxyphenyl)-piperazinyl-1]-propionate (prepared according to Example 1b), after the ring closure in ethanolic hydrochloric acid, a reaction mixture which is stirred into ice water. The mixture is shaken out with methylene chloride (a sample shows that the desired product is extracted as monohydrochloride) and the organic phase is dried with anhydrous magnesium sulfate and acidified with ethereal hydrochloric acid to give the dihydrochloride of 2-{2-[4-(2-methoxyphenyl)-piperazinyl-1]-ethyl}-5,7-dimethyl-4-oxo-4H-1-benzopyran; m.p. 183° C. Yield of the first batch 13.3 g.

The aqueous acidic phase of the first extraction is neutralized with sodium bicarbonate, extracted with methylene chloride and the organic phase, after drying with anhydrous sodium sulphate, is acidified with ethereal hydrochloric acid. In this way, there is obtained a second batch of 7.9 g (m.p. 182° – 183° C) which is also analytically identical with the first batch.

Thus, the total yield is 21.2 g of dihydrochloride (89.5% of theory).

EXAMPLE 19

2-{2-[4-(2-Methoxyphenyl)-piperazinyl-1]-ethyl}-5-(2-hydroxypropoxy)-4-oxo-4H-1-benzopyran (a) 2-Hydroxy-6-(2-hydroxypropoxy)-acetophenone 30 g 2,6-dihydroxyacetophenone are heated in 60 ml dioxane with 12 g 1,2-epoxypropane, after the addition of a few drops of Triton B, for 48 hours in a glass autoclave (120° C. oil bath temperature). Subsequently, the reaction mixture is evaporated, the residue is taken up in 2N aqueous sodium hydroxide solution (disubstituted product is removed by diethyl ether extraction) and, after the addition of 5N hydrochloric acid, extracted with chloroform. The evaporation residue of the organic phase is subsequently distilled in a vacuum to give 21.4 g (51.7% of theory) 2-hydroxy-6-(2-hydroxypropoxy)-acetophenone; b.p. 151°–155° C/0.01 mm Hg.

(b) 2-Hydroxy-6-[2-(tetrahydropyran-2-yloxy)-propoxy]-acetophenone 8.4 g (0.04 mol) of the 2-hydroxypropoxy derivative prepared according to Example 19a are mixed with 25 ml 2,3-dihydropyran. After the addition of a drop of polyphosphoric acid, the starting material dissolves, with warming. The reaction mixture is stirred for 1 hour at ambient temperature, taken up in diethyl ether and shaken out with aqueous sodium bicarbonate solution. The evaporation residue of the ethereal layer consists, apart from a little starting phenol, of the greater part of the desired mono-tetrahydropyran-2-yloxy compound (thin layer chromatogram, ferric chloride detection; solvent isopropanol/butyl acetate/water/concentrated aqueous ammonia solution = 50:30:15:5) and of the bis-substituted compound, 2-(tetrahydropyran-2-yloxy)-6-[2-(tetrahydropyran-2-yloxy)-propoxy]-acetophenone, which is obtained in the form of a viscous oil.

(c) Chromone ring closure

A sample of the 2-hydroxy-6-(2-hydroxypropoxy)-acetophenone, protected with tetrahydrofuran, obtained according to Example 19b, is condensed, as in Example 1, with ethyl 3-[4-(2-methoxyphenyl)-piperazinyl-1]-propionate in the presence of sodium hydride and subsequently cyclized in isopropanolic hydrochloric acid. After the usual working up, there is obtained the dihydrochloride of 2-{2-[4-(2-methoxyphenyl)-piperazinyl-1]-ethyl}-5-(2-hydroxypropoxy)-4-oxo-4H-1-benzopyran; m.p. 166°–168° C.

The structure is confirmed spectro-analytically, as in Example 1.

EXAMPLE 20

2-{2-[4-(2-Methoxyphenyl)-piperazinyl-1]-ethyl}-5-oxiranyl-methyl)-4-oxo-4H-1-benzopyran 0.24 g (0.01 mol) sodium hydride are suspended in 25 ml hexamethyl-phosphoric acid triamide (HMPT) and slowly mixed with a solution of 3.8 g (0.01 mol) 2-{2-[4-(2-methoxyphenyl)-piperazinyl-1]-ethyl}-5-hydroxy-4-oxo-4H-1-benzopyran (preparation see Example 15) in 25 ml HMPT. After stirring for one hour at ambient temperature, foaming of the reaction mixture decreases. Subsequently, the reaction mixture is mixed dropwise with 4.11 g (0.03 mol) epibromohydrin, stirred for 1 hour at ambient temperature and then for 2 hours at 40°–45° C. The reaction mixture is thereafter stirred into ice water and the precipitate filtered off with suction. The solid material is taken up in chloroform, shaken out with water, dried, with the addition of charcoal, and evaporated. There are obtained 2.4 g (55% of theory) 2-{2-[4-(2-methoxyphenyl)-piperazinyl-1]-ethyl}-5-(oxiranyl-methyl)-4-oxo-4H-1-benzopyran in the form of a yellowish powder. The melting point is not sharp (about 130° C), since traces of HMPT are still present (detection in the mass spectrum).

EXAMPLE 21

2-{2-[4-(3-Trifluoromethyl-phenyl)-piperazinyl-1]-ethyl}-5-methoxy-4-oxo-4H-1-benzopyran (a) Analogously to Example 1b, 25 g (1-(3-trifluoromethyl-phenyl)-piperazine (commercial product of EMKA Chemie) are reacted with an equimolar amount of ethyl acrylate in 80 ml ethanol and the reaction product is distilled in a vacuum. There are obtained 30.3 g (84.53% of theory) ethyl 3-[4-(3-trifluoromethyl-phenyl)-piperazinyl-1]-propionate in the form of a colorless oil; b.p. 158°–159° C/0.1 mm Hg.

(b) Chromone ring closure

In the manner described in Examples 1–3, 3.6 g (0.15 mol) sodium hydride, 8.3 g (0.05 mol) 2-methoxy-6-hydroxy-acetophenone and 18.16 g (0.055 mol) of the basic ester obtained according to Example 21a are reacted in 100 ml tetrahydrofuran. After ring closure has taken place in ethanolic hydrochloric acid, the reaction mixture is stirred into ice water and shaken out with methylene chloride. All of the basic material remains in the aqueous acidic solution. After partial neutralization with sodium bicarbonate, a gel-like precipitate is obtained which can be dissolved in methylene chloride, with the addition of a little methanol. From the organic layer, there is obtained, by evaporation, a crude hydrochloride which is triturated with a little isopropanol. There are obtained 16.2 g (69.1% of theory) 2-{2-[4-(3-trifluoromethyl-phenyl)-piperazinyl-1]-ethyl}-5-methoxy-4-oxo-4H-1-benzopyran in the form of the monohydrochloride; m.p. 206°–207° C.

The structure is confirmed not only by IR, UV and NMR spectra but also by the mass spectrum (M$^+$432).

EXAMPLE 22

2-{2-[4-(2-Trifluoromethyl-phenyl)-piperazinyl-1]-ethyl}-5-methoxy-4-oxo-4H-1-benzopyran As described in Example 21 for the 3-trifluoromethyl derivative, 1-(2-trifluoromethyl-phenyl)-piperazine is reacted with ethyl acrylate to give the basic propionic acid derivative (yield 76% of theory; b.p. 160°–168° C/0.01 mm Hg) and subsequently, with the same batch size, this is reacted in 80 ml dioxane with 2-methoxy-6-hydroxy-acetophenone, followed by ring closure in ethanolic hydrochloric acid to give, in 61% yield, 2-{2-[4-(2-trifluoromethyl-phenyl)-piperazinyl-1]-ethyl}-5-methoxy-4-oxo-4H-1-benzopyran. The isolated hydrochloride has a melting point of 143°–146° C and consists of a mixture of mono- and dihydrochloride of the pure base. After recrystallizing once from isopropanol, there is obtained the monohydrochloride which melts, with decomposition, at 198°–199° C.

EXAMPLE 23

2-{2-[4-(4-Hydroxyphenyl)-piperazinyl-1]-ethyl}-5-methoxy-4-oxo-4H-1-benzopyran (a) Analogously to Example 1b, 25 g (0.14 mol) 1-(4-hydroxyphenyl)-piperazine (commercial product of EMKA Chemie) are reacted under an atmosphere of nitrogen with 15.2 ml ethyl acrylate in 200 ml ethanol. After a reaction time of one hour, the thin layer chromatogram shows that only partial reaction has taken place in the suspension. The reaction mixture is further stirred overnight and the fresh precipitate filtered off with suction. There are obtained 34.7 g (88.93% of theory) ethyl 3-[4-(4-hydroxyphenyl)-piperazinyl-1]-propionate; m.p. 118°–120° C.

(b) 15.3 g (0.055 mol) of the ester obtained in Example 23a are heated for 3 hours on the water-bath to 60° C with 20 ml tetrahydrofuran, after the addition of one drop of polyphosphoric acid. The reaction mixture is then partly evaporated, taken up in chloroform and shaken out with aqueous sodium bicarbonate solution and the organic phase is dried and evaporated. There remain (17.2 g of a product which, in addition to the phenolic starting material, contains the desired ethyl 3-[4-(4-tetrahydropyran-2-yloxy-phenyl)-piperazin-1-yl]-propionate (thin layer chromatogram, chloroform-methanol = 9:1), which can be further reacted in this form.

(c) Chromone synthesis

Analogously to Examples 1–3, the propionic acid ester obtained in Example 23b, partially protected by the tetrahydropyranyl radical, is reacted with 8.3 g (0.05 mol) 2-methoxy-6-hydroxy-acetophenone in 120 ml dioxane with 0.15 mol sodium hydride as condensation agent and the chromone ring subsequently closed with ethanolic hydrochloric acid. The reaction mixture is poured on to ice and extracted with methylene chloride. The strongly acidic aqueous layer is then neutralized with sodium bicarbonate and again shaken out with methylene chloride. There are obtained 12.2 g (62.17% of theory) 2-{2-[4-(4-hydroxyphenyl)-piperazinyl-1]-ethyl}-5-methoxy-4-oxo-4H-1-benzopyran in the form of the pure base; m.p. 202°–204° C. The corresponding hydrochloride has a melting point of 196° C (precipitated from chloroform/isopropanol).

The same compound is obtained by the reaction of the unprotected ethyl 3-[4-(4-hydroxyphenyl)-piperazinyl-1]-propionate with 2-methoxy-6-hydroxy-acetophenone in dioxane, with the addition of about 10% hexamethylphosphoric acid triamide at a reaction temperature of 80° C.

The foregoing compounds can be used as such or they can be converted to salts with pharmacologically acceptable acids.

With respect to the proper dosage and methods of application for the instant compounds, these are comparable to those for the commercially known compound "Fragivix", i.e. 2-ethyl-3-(4'-hydroxybenzoyl)-benzofuran. They can also be administered per os. The instant compounds make possible comprehensive therapy of acute as well as chronic phlebological and capillary afflications as well as varicose syndromes. The instant compounds retard reactions leading to edemas and swellings, including those of allergic origin.

The typical daily dosage of 10 to 300 mg results in reducing or eliminating the above afflications, commonly within some days. A preferred dosage is 30–100 mg.

The superior activity of the novel compounds is shown by comparing the inhibition of the passive cutaneous anaphylactic reaction in rats produced by injection of serum containing reaginic antibodies to egg albumin. Diethylcarbamazin, i.e. 1-diethylcarbamoyl-4-methylpiperazine, was used as a comparison compound. Specifically, tests were run as follows:

Serum containing reaginic (IgE-like) antibody to egg albumin was prepared by injecting rats intramuscularly with 0.1 ml of a solution of the antigen (10 mg/ml) in saline together with 0.5 ml of Bordetella pertussis vaccine (Behring; 2 × 10¹⁰ organisms/ml). 9–14 days later the animals were bled from the abdominal aorta; the serum was pooled and stored at −20° C until required. The titer of the serum, i.e. the highest dilution inducing passive cutaneous anaphylaxis (PCA) in the rat following a 48-hour latent period, was between 1:8 and 1:32. For use in these experiments the serum was diluted 1:24. The reaginic nature of the antibody was demonstrated by its ability to induce PCA with a latent period in excess of 1 day and also by abolition of its PCA activity by heating it at 56° C for 1 hour.

The animals were anesthetized with 2,2-dichloro-1,1-difluoroethyl-methyl ether, sold under the trademark Penthrane, and were sensitized by injecting 0.1 ml of the antiserum into the shaved abdominal flanks. After 48 hours for reaginic PCA, the animals were given an intravenous injection of 1 ml of saline solution containing 0.5% by weight of egg albumin and 0.25% by weight of Evans blue.

After having killed and exsanguinated the animals, the size in square millimeters and the intensity, in arbitary scores, of the resulting blue spot were determined. The product of these two parameters was used to determine the degree of the reaction and the degree of reaction with no active material was taken as the standard against which to measure % inhibition of the anaphylactic reaction.

Six animals were used per dose level and for control.

In some instances the test material was injected intravenously (i.v.) immediately before the antigen, using a solution in water containing 0.5% HCl and 2% of dimethylformamide, and in other instances per os 40 minutes before the antigen. The volume of the application was varied to give the indicated dosage of active material. The results obtained were as follows:

PCA Reaction in Rats Induced by Reaginic Antibodies (Ovalbumin 2 × cryst. and Bord. pertussis 2 × 10¹⁰)

| Application of the compounds: per os 40 min. before Antigen | | | | |
|---|---|---|---|---|
| | i.v. immediately before Antigen | | | |
| | i.v. | | per os | |
| Active Material | dose, mg/kg | inhibition PCA, % | dose, mg/kg | inhibition PCA, % |
| Diethyl-carbamazin | 60.0 | 58 | 60.0 | 10 |
| Ex. 1 | 0.86 | 50 | 1.0 | 50 |
| Ex. 3 | 1.5 | 35 | 1.5 | 35 |
| Ex. 6 | 1.5 | 60 | 1.5 | 42 |
| Ex. 7 | — | — | 3.0 | 53 |
| Ex. 9 | — | — | 1.5 | 36 |
| Ex. 16 | 1.6 | 50 | 3.0 | 50 |
| Ex. 18 | 0.75 | 54 | — | — |
| Ex. 19 | 0.75 | 50 | 3.0 | 49 |

These pharmacological data show that the novel compounds exert a far stronger antianaphylactoid activity than Diethylcarbamazin whether administered intravenously or per os.

It will be appreciated that the instant specification and examples are set forth by way of illustration and not limitation, and that various modifications and changes may be made without departing from the spirit and scope of the present invention.

We claim:

1. A benzopyrone of the formula

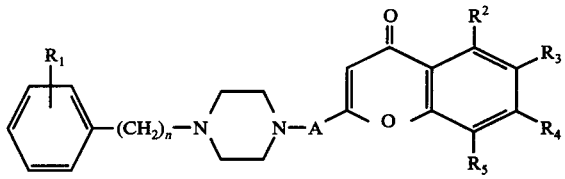

wherein
$R_1$ is a hydrogen or halogen atom or hydroxyl, lower alkyl, alkoxy, alkylthio or trifluoromethyl,
$R_2$, $R_3$, $R_4$ and $R_5$ each independently is hydrogen, a halogen atom, hydroxyl, lower alkyl or lower alkoxy, or lower alkyl or lower alkoxy substituted by at least one of hydroxyl, halogen, mesyloxy or tosyloxy or by an oxirane, dioxane or dioxolane ring,
A is lower alkylene, and $n$ is 0, 1 or 2, or a salt thereof with a pharmacologically compatible acid.

2. A benzopyrone according to claim 1, wherein $R_1$ is a hydrogen, fluorine, chlorine or bromine atom, or hydroxyl, trifluoromethyl, or alkyl, alkoxy or alkylthio containing up to 3 carbon atoms, $R_2$, $R_3$, $R_4$ and $R_5$ each independently is a hydrogen, fluorine, chlorine or bromine atom, or hydroxyl, alkyl or alkoxy containing up to 3 carbon atoms, or alkyl or alkoxy radical containing up to 3 carbon atoms and substituted by at least one of hydroxyl, fluorine, chlorine, bromine, mesyloxy, tosyloxy, oxiranyl, dioxanyl and dioxolanyl, A is alkylene of up to 4 carbon atoms, and $n$ is 0 or 1.

3. A benzopyrone or a salt thereof according to claim 1 wherein said benzopyrone is 2-{2-[4-(2-methoxyphenyl)-piperazinyl-1]-ethyl}-5-methoxy-4-oxo-4H-1-benzopyran of the formula

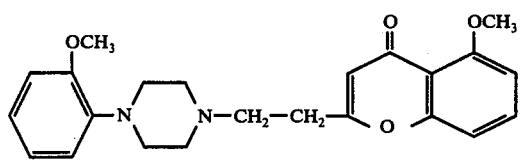

4. A benzopyrone or a salt thereof according to claim 1 wherein said benzopyrone is 2-{2-[4-(3-methoxyphenyl)-piperazinyl-1]-ethyl}-5-methoxy-4-oxo-4H-1-benzopyran of the formula

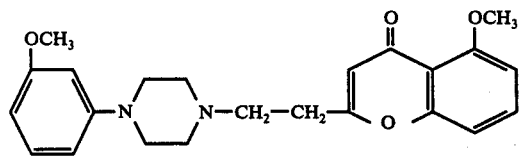

5. A benzopyrone or a salt thereof according to claim 1 wherein said benzopyrone is 2-{2-[4-(2-methylphenyl)-piperazinyl-1]-ethyl}-5-methoxy-4-oxo-4H-1-benzopyran of the formula

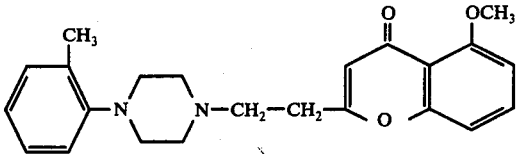

6. A benzopyrone or a salt thereof according to claim 1 wherein said benzopyrone is 2-{2-[4-(2-methoxyphenyl)-piperazinyl-1]-ethyl}-5-(2,3-dihydroxypropoxy)-4-oxo-4H-1-benzopyran of the formula

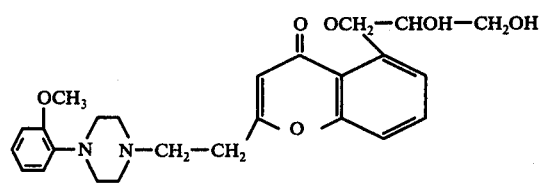

7. A benzopyrone or a salt thereof according to claim 1 wherein said benzopyrone is 2-{2-[4-(2-methoxyphenyl)-piperazinyl-1]-ethyl}-5-(2-hydroxypropoxy)-4-oxo-4H-1-benzopyran of the formula

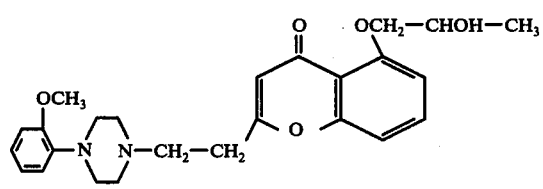

8. An anti-allergic composition comprising an anti-allergically effective amount of at least one benzopyrone according to claim 1, in admixture with a diluent.

9. A method of combating allergy in a patient comprising administering to said patient an anti-allergically effective amount of at least one benzopyrone according to claim 1.

10. The method according to claim 9, wherein such benzopyrone is

2-{2-[4-(2-methoxyphenyl)-piperazinyl-1]-ethyl}-5-methoxy-4-oxo-4H-1-benzopyran, 2-{2-[4-(3-methoxyphenyl)-piperazinyl-1-ethyl}-5-methoxy-4-oxo-4H-1-benzopyran, 2-{2-[4-(2-methylphenyl)-piperazinyl-1]-ethyl}-5-methoxy-4-oxo-4H-1-benzopyran, 2-{2-[4-(2-methoxyphenyl)-piperazinyl-1]-ethyl}-5-(2,3-dihydroxypropoxy)-4-oxo-4H-1-benzopyran, 2-{2-[4-(2-methoxyphenyl)-piperazinyl-1]-ethyl}-5-(2-hydroxypropoxy)-4-oxo-4H-1-benzopyran or a salt thereof with a pharmacologically compatible acid.

* * * * *